US012728249B2

(12) United States Patent
Quan et al.

(10) Patent No.: US 12,728,249 B2
(45) Date of Patent: Sep. 8, 2026

(54) HIGH-PERFORMANCE MICRO-NEEDLE ARRAY

(71) Applicant: COSMED PHARMACEUTICAL CO., LTD., Kyoto-city (JP)

(72) Inventors: Ying-shu Quan, Kyoto-city (JP); Ying-zhe Li, Kyoto-city (JP); Kenji Kajiyama, Kyoto-city (JP); Mio Saito, Kyoto-city (JP); Hirofumi Yamashita, Kyoto-city (JP); Fumio Kamiyama, Kyoto-city (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 752 days.

(21) Appl. No.: 17/999,429

(22) PCT Filed: May 24, 2021

(86) PCT No.: PCT/JP2021/019584
§ 371 (c)(1),
(2) Date: Nov. 21, 2022

(87) PCT Pub. No.: WO2021/241486
PCT Pub. Date: Dec. 2, 2021

(65) Prior Publication Data

US 2023/0233823 A1 Jul. 27, 2023

(30) Foreign Application Priority Data

May 25, 2020 (JP) ................................ 2020-090925

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0023* (2013.01)

(58) Field of Classification Search
CPC ...... A61M 37/0015; A61M 2037/0046; A61M 2037/0023; A61M 2037/0053; A61M 2037/0061
See application file for complete search history.

(56) References Cited

U.S. PATENT DOCUMENTS 6,050,988 A * 4/2000 Zuck ................. A61B 5/14514 604/20
2007/0004989 A1 1/2007 Dhillon
(Continued)

FOREIGN PATENT DOCUMENTS

CN 101829394 A 9/2010
CN 102311091 A 1/2012
(Continued)

OTHER PUBLICATIONS

Translation of JP 2009240410A (Year: 2009).*
(Continued)

*Primary Examiner* — Nilay J Shah
(74) *Attorney, Agent, or Firm* — Cheng Law Group, PLLC

(57) ABSTRACT

Provided is a micro-needle array in which all fine needles can be more easily inserted into the skin regardless of positions where the fine needles of the micro-needle array are located on a substrate. The micro-needle array includes: a substrate; and a plurality of micro-needles arranged on one surface of the substrate. Tip parts of the plurality of micro-needles have a height difference, and the micro-needles have a needle length of 80 μm or more and 2000 μm or less. The height difference of the plurality of micro-needles is preferably based on unevenness of the substrate.

11 Claims, 6 Drawing Sheets

(56) References Cited

U.S. PATENT DOCUMENTS

2010/0022864 A1 1/2010 Cordero et al.
2011/0288484 A1* 11/2011 Kendall ............... A61K 9/0021 604/173
2012/0004614 A1 1/2012 Stumber et al.
2014/0296683 A1 10/2014 Cordero et al.
2015/0209563 A1 7/2015 Amir
2015/0335870 A1 11/2015 Quan et al.
2016/0151616 A1 6/2016 Berry et al.
2016/0279401 A1 9/2016 Schwab et al.
2017/0304603 A1* 10/2017 Kato .................... A61B 17/205
2018/0229017 A1 8/2018 Schwab et al.
2019/0038550 A1 2/2019 Quan et al.
2019/0117948 A1 4/2019 Berry et al.
2019/0134368 A1 5/2019 Nagai et al.
2019/0344062 A1 11/2019 Quan et al.
2021/0016072 A1 1/2021 Quan et al.
2022/0241569 A1 8/2022 Quan et al.

FOREIGN PATENT DOCUMENTS

CN 105407957 A 3/2016
JP 2003-238347 A 8/2003
JP 2009240410 A * 10/2009 ........ A61M 37/0015
JP 2009-273872 A 11/2009
JP 2010-29634 A 2/2010
JP 5285943 B2 9/2013
JP 2014-28108 A 2/2014
JP 2015-109963 A 6/2015
JP 2016-175853 A 10/2016
JP 2017-47075 A 3/2017
JP 2017-74196 A 4/2017
JP 2017-137311 A 8/2017
JP 2017-185162 A 10/2017
JP 2018-108375 A 7/2018
JP 2019-103822 A 6/2019
JP 2019-205527 A 12/2019
JP 2021-3547 A 1/2021
WO WO-2016/114213 A1 7/2016
WO WO-2017/208962 A1 12/2017
WO WO-2018/124290 A1 7/2018
WO WO-2020262473 A1 * 12/2020 ........ A61M 37/0015

OTHER PUBLICATIONS

Translation of WO2020262473 A1 (Year: 2020).*
The First Office Action for the Application No. 202180033951.7 from The State Intellectual Property Office of the People's Republic of China dated Mar. 29, 2025.
Written Opinion of the International Searching Authority (PCT/ISA/237) for Application No. PCT/JP2021/019584 mailed Aug. 3, 2021 (English Translation mailed Dec. 8, 2022).
Guang, Yan et al., "Evaluation needle length and density of microneedle arrays in the pretreatment of skin for transdermal drug delivery", International Journal of Pharmaceutics, 2010, vol. 391, pp. 7-12.
Lhernould, Marion Sausse et al., "Hollow polymer microneedles array resistance and insertion tests", International Journal of Pharmaceutics, 2015, pp. 152-157.
Quan, Ying-shu et al., "The Course of Productization of Microneedle", The Archives of Practical Pharmacy, The Academy of Pharmaceutical Science and Technology, 2009, vol. 69, No. 4, pp. 272-276.
International Search Report for the Application No. PCT/JP2021/019584 mailed Aug. 3, 2021.
Written Opinion of the International Searching Authority (PCT/ISA/237) for Application No. PCT/JP2021/019584 mailed Aug. 3, 2021.
Supplementary European Search Report for the Application No. 21 812 732.2 dated Jun. 6, 2024.
The Second Office Action for the Application No. 202180033951.7 from The State Intellectual Property Office of the People's Republic of China dated Sep. 23, 2025.
Notification of Reasons for Refusal for the Application No. 2021-086713 from Japan Patent Office mailed Jun. 25, 2025.
Examination Report for the Australian Patent Application No. 2021-280068 from Australian Patent Office mailed Feb. 6, 2026.

* cited by examiner

[FIG. 1]
(A)
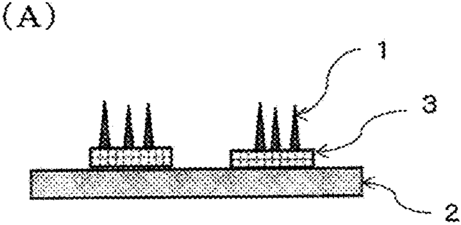
(B)
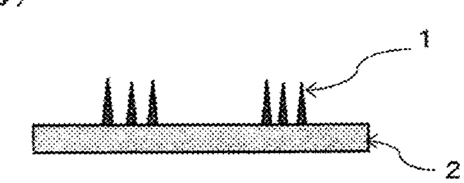
[FIG. 2]
(A)
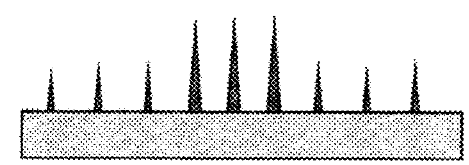
(B)
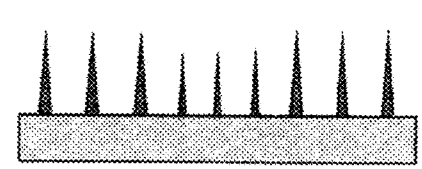
[FIG. 3]
(A)
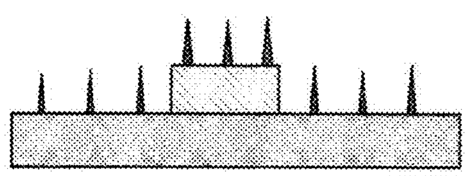
(B)
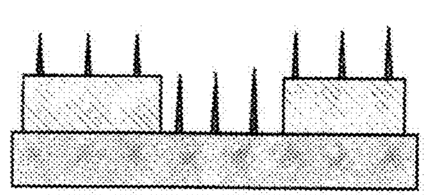
(C)
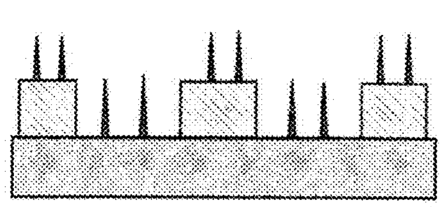

[FIG. 4]
(A)
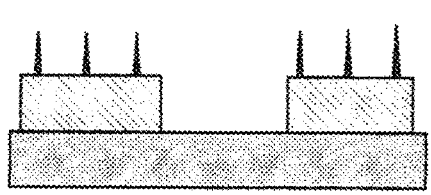
(C)
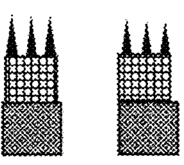
(B)
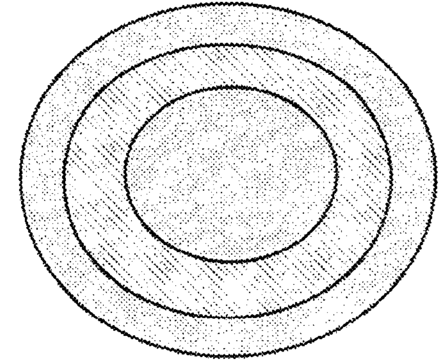
(D)
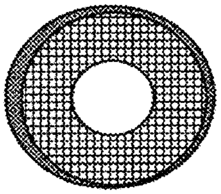
[FIG. 5]
(A)
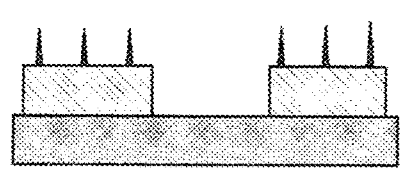
(B)
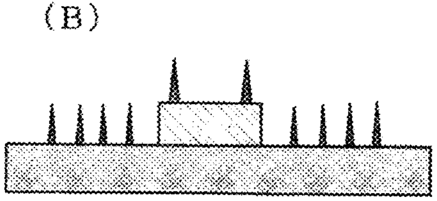
[FIG. 6]
(A)
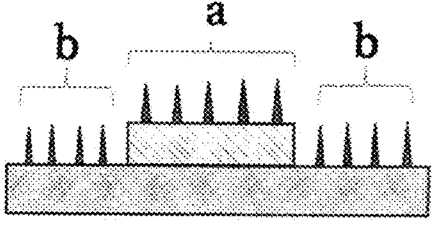
(B)
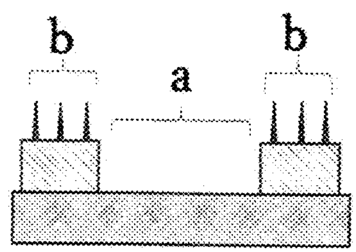

[FIG. 7.]
(A)
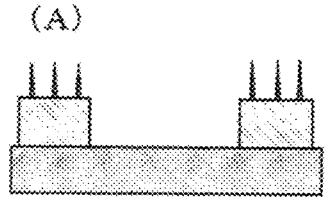
(B)
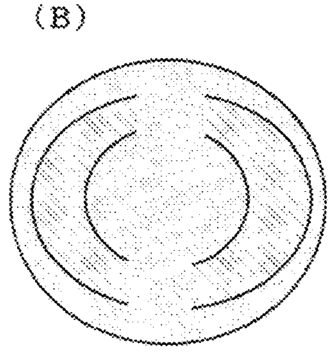
(C)
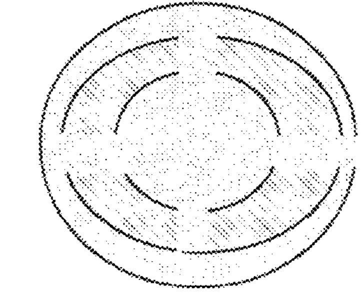
(D)
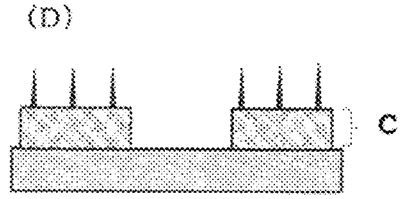
[FIG. 8.]
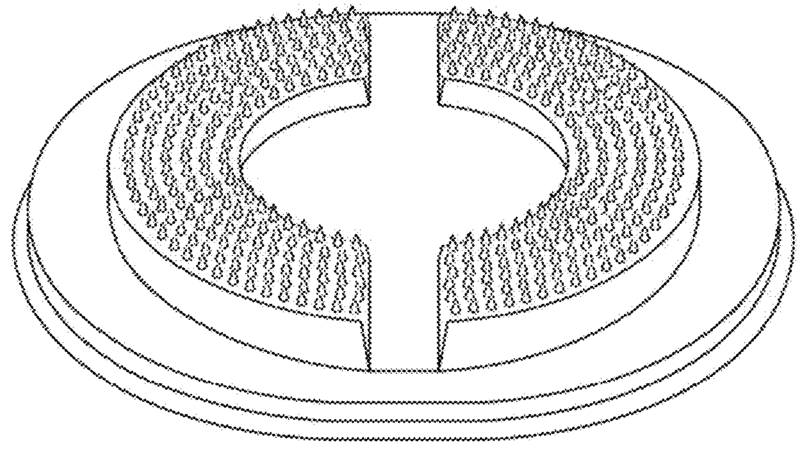

[FIG. 9.]
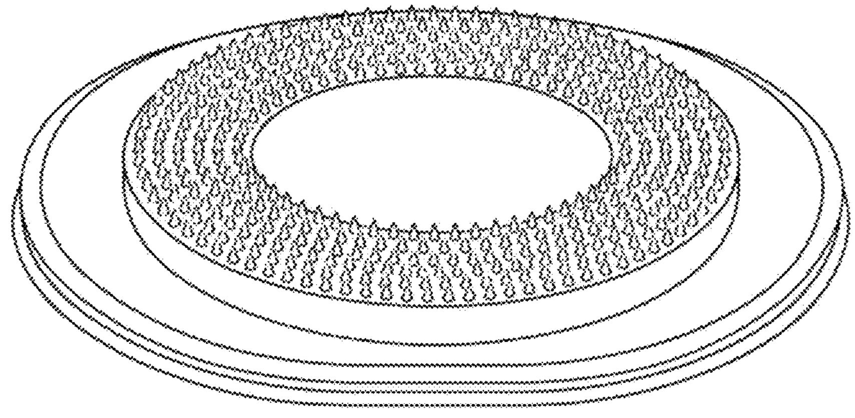
[FIG. 10.]
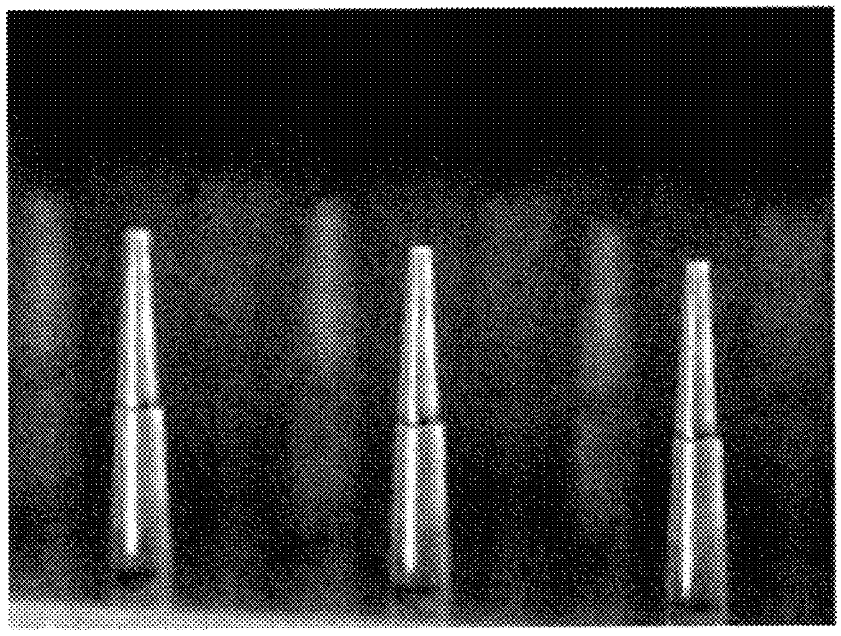

[FIG. 11]
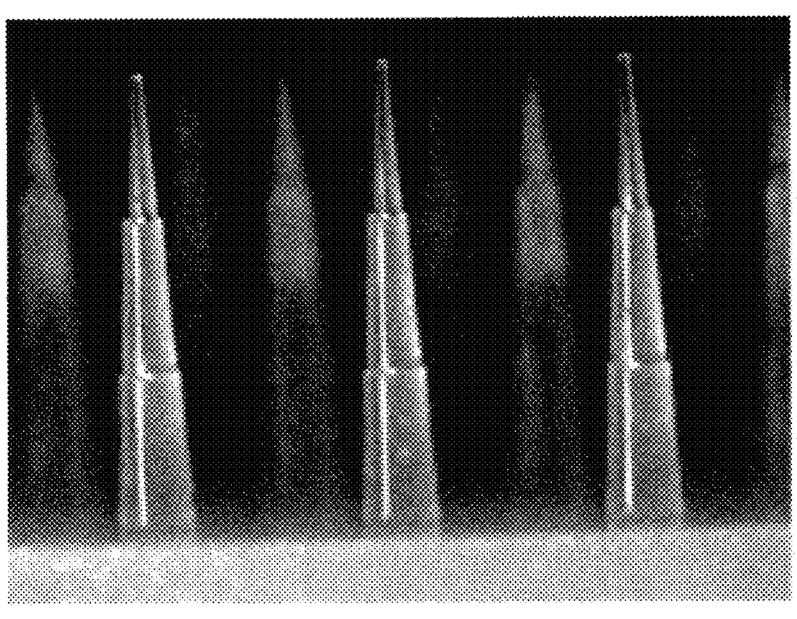
[FIG. 12]
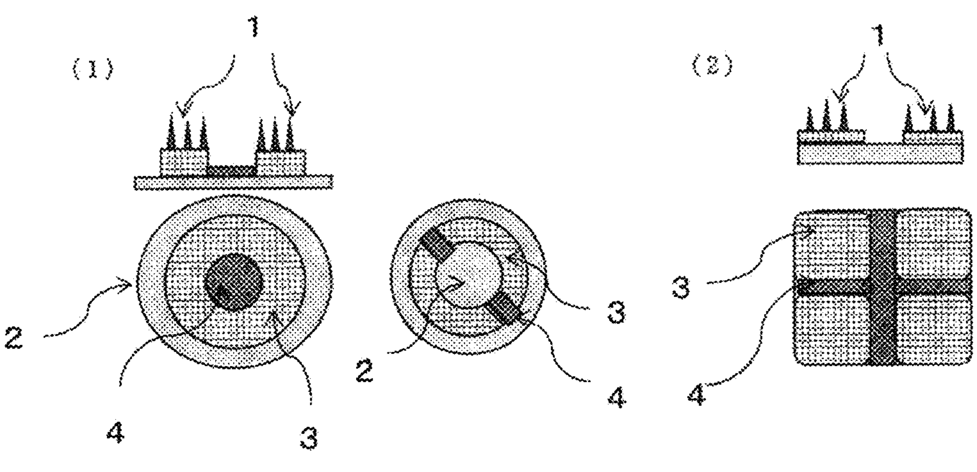
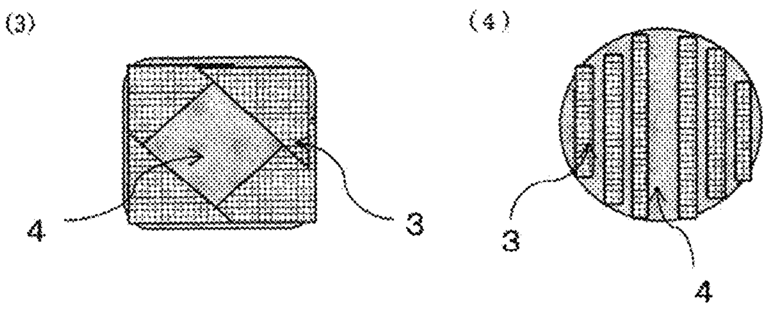

[FIG. 13]
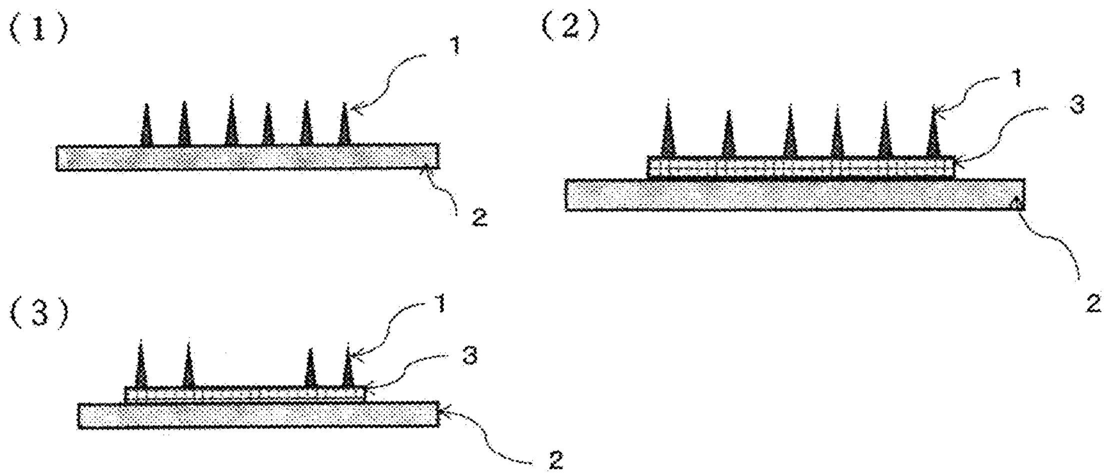

HIGH-PERFORMANCE MICRO-NEEDLE ARRAY

TECHNICAL FIELD

The present invention relates to a technique of a micro-needle array including needles having tip parts having a height difference.

BACKGROUND ART

As a method for administering a drug into a human body, oral administration and transdermal administration are often used. A transdermal administration method without pain using a micro-needle array has been recently attracting attention (Non-Patent Document 1).

Perforation into stratum corneum by using a minute needle, that is, a micro-needle, can remarkably improve drug permeation efficiency compared with an application method. An article in which a large number of micro-needles are integrated on a substrate is a micro-needle array. A product in which an adhesive sheet for adhering the micro-needle array to a skin, and a release sheet for protecting an adhesive surface and the like are added to the micro-needle array to facilitate its use is called a micro-needle patch.

As the material of the micro-needle, metal or silicon has been initially used, but thereafter, various polymer materials have been attracting attention from the viewpoint of processability. In particular, when a micro-needle is produced using a substance that disappears by metabolism in the body such as a carbohydrate as a material, an accident does not occur even if the needle breaks and remains in the skin.

In micro-needle patches known in Patent Documents and Academic Literatures and the like, a bottom surface on which a micro-needle array stands is a plane, and fine needles having a uniform length stand vertically at a uniform density on the bottom surface. Micro-needle patches which have been produced by the present inventors and have been filed for patent up to now are also included in the category (Patent Documents 1 and 2). It is described that the micro-needles disclosed in Patent Documents 1 and 2 have a (circular) cone shape, a (circular) truncated cone shape, or a konide shape, and the pitch between the micro-needles is preferably 0.4 to 1.0 mm. Various improvements have been made regarding a micro-needle drug product and a method for producing the same, which have been filed for patent in recent years, for the purpose of ensuring puncture into a skin with micro-needles (Patent Documents 3 and 4), the purpose of making micro-needles uniformly carry a drug (Patent Documents 5 and 6), and the like.

Patent Document 3 describes that a needle-shaped body device (micro-needle array) is arranged such that a protrusion has a pyramid shape and a blade formed by two side surfaces of the pyramid shape is directed to a tangential line of a circle having a predetermined position on the surface of a substrate as a center point.

Patent Document 4 describes that in a dissolvable micro-needle drug product containing hyaluronic acid and the like, the distance between adjacent needle parts is substantially equal, about 1 to 10 needles are arranged per 1 mm, and the density of the needle parts is preferably 100 to 10000 needles per 1 $cm^2$.

It is described that a micro-needle array produced by the production method of the micro-needle array of Patent Document 5 preferably has a needle density of 1 to 200 needles/$cm^2$ from the viewpoint of being able to administer a predetermined drug without pain.

It is described that a micro-needle device produced by the production method of the micro-needle device of Patent Document 6 has a row of needles provided at intervals to have a density of about 1 to 10 needles per 1 mm, separated from each other by an equal distance with respect to the space of the needles in the row, and has a needle density of 100 to 10000 needles per 1 $cm^2$.

As described above, the micro-needles of Patent Documents 1, 2, and 4 to 6 are provided at equal intervals on the substrate, and the needle density per unit area is also constant. Meanwhile, Patent Document 3 discloses a needle-shaped body device (micro-needle array) including a substrate having a plane, wherein blades of the needle-shaped body are arranged in a tangential direction of a circle, and an arrangement pattern thereof is a radial shape from a center of the circle toward an outer periphery (FIG. 3), a spiral shape spreading from the center of the circle toward the outer periphery (FIG. 4), a linear shape eccentric from a central axis (FIG. 5(*a*)), and a plurality of non-line-symmetric linear shapes (FIG. 5(*b*)) and the like. However, the blades adjacent to each other in the tangential direction are at equal intervals, and are arranged substantially uniformly in balance over the entire substrate of the needle-shaped body.

Regarding the needle density of the micro-needles and the skin permeability of the needles, it is described that a micro-needle array having 900 needles/$cm^2$ is poor in skin permeability compared with a micro-needle array having 400 needles/$cm^2$ (Non-Patent Document 2).

In the patent application (Japanese Patent Application No. 2019-219179) previously filed by the present inventors, there is provided a micro-needle array in which a needle interval and a needle density of micro-needles are different between a peripheral part and a central part of a substrate. However, in the patent application, the substrate has the same height (thickness) in both the central part and the peripheral part, and has no height difference.

PRIOR ART DOCUMENT

Patent Document

Patent Document 1: JP 2009-273872 A
Patent Document 2: JP 2010-029634 A
Patent Document 3: JP 2017-074196 A
Patent Document 4: JP 2016-175853 A
Patent Document 5: JP 2015-109963 A
Patent Document 6: JP 2017-047075 A

Non-Patent Document

Non-Patent Document 1: Ying-shu Quan and Fumio Kamiyama, "The Course of Productization of Micro-needle", The Archives of Practical Pharmacy, The Academy of Pharmaceutical Science and Technology, Japan, July 2009, Vol. 69, No. 4, p. 272-276

Non-Patent Document 2: G. Ya, et al., Evaluation needle length and density of microneedle arrays in the pretreatment of skin for transdermal drug delivery, International Journal of Pharmaceutics 391 (2010) 7-12

SUMMARY OF THE INVENTION

Problem to be Solved by the Invention

When a conventional micro-needle patch is administered to an animal skin for a test, the micro-needle patch is struck at a high speed from behind the micro-needle patch by an applicator, and energy due to the impact is applied to the micro-needle patch to achieve the insertion of fine needles into the skin. The surface of the applicator to impact the micro-needle patch known to date is a plane. In the course of administration to an animal or human using such a system, the present inventors have noticed the following phenomenon.

1. When the density of the needles is too high, insertion into animal and human skin becomes difficult (phenomenon 1).

According to the findings by the present inventors, it tends to be difficult for the needles to penetrate the skin when the needle density is more than 1500 needles/cm$^2$.

Prior to the present inventors, Non-Patent Document 2 describes that a micro-needle array having 900 needles/cm$^2$ is poor in skin permeability compared with a micro-needle array having 400 needles/cm$^2$.

2. In the detailed analysis of phenomenon 1, it is more difficult to insert the needles into the skin in the central part of the micro-needle array than in the peripheral part (phenomenon 2).

Patent Application (Japanese Patent Application No. 2019-219179) is the micro-needle array based on the design idea that the needle density in the peripheral part of the array is higher than that in the central part based on the observation of phenomenon 2. This eliminates the problem that makes it difficult for the fine needle located in the central part of the micro-needle array to be inserted into the skin.

When the micro-needle array is brought into contact with and pressed against the skin, the surface of the skin is recessed along the array, whereby the micro-needle array cannot be uniformly inserted into the skin, which also causes a problem that a difference in the depth of the insertion occurs. An object of the present invention is to provide a micro-needle array in which all fine needles can be more easily inserted into the skin regardless of positions where the fine needles of the micro-needle array are located on a substrate.

Means for Solving the Problem

3. In further studies, the present inventors focused on the shape of the substrate of the micro-needle array, and obtained a preliminary result: the surface of the substrate having a high needle density is heightened (the thickness of the substrate is increased) and the surface of the substrate having a low needle density or no needles is lowered (the thickness of the substrate is decreased) to apply a height difference to the substrate (apply unevenness to the shape of the substrate), which is advantageous for the insertion of the micro-needles into the skin (phenomenon 3).

In order to further improve the insertability of the micro-needles into the skin, the present inventors performed a model experiment concerning phenomenon 3 (apply a height difference to the substrate (applying unevenness to the shape of the substrate)) using a parafilm instead of the skin. Eight parafilms (thickness: 140 μm) were stacked, and two types of micro-needle arrays were administered thereto. When the cross section of a first micro-needle array (product of the present invention, FIG. 1A) is observed, a part of the substrate is a convex part, and the height of the convex part is 1000 μm. Micro-needles stand side by side only on the convex part. When the product of the present invention was observed from above, the product was a circular micro-needle array in which the surface of the convex part of the substrate was concentric on the substrate. A central part surrounded by the convex part has the same height as that of the plane of the substrate, and the micro-needles are not present on the central part. The product of the present t invention had a substrate diameter of 10 mm and a needle length of 900 μm. A second micro-needle array (comparative product, FIG. 1B) was micro-needle patch in which a substrate had a constant thickness (no unevenness), and the total number, density, and positions on the substrate of micro-needles were designed to be substantially equal to those of the product of the present invention. The micro-needle patch was impacted by an applicator (WO 2018/124290 or JP 2017-185162 A) to examine the insertion behavior of the micro-needles into the parafilm in detail. It is already known in the literature (Int. J. Pharmaceutics 480 (2015) 152-157) to analyze the insertion behavior of the micro-needles using the parafilm as a skin substitute, and there is a reliable correlation with the insertion behavior into skin.

As a result, the present inventors have found that the micro-needle array having the micro-needles on the convex part of the substrate higher by 1000 μm than the plane of the substrate has an increased total number of insertion needles as compared with that of a micro-needle array in which a substrate has a constant thickness (no unevenness). The present inventors have conceived of achieving a desired object by applying a height difference to the tip parts of the needles brought into contact with the skin and providing the convex part according to the object, and have completed the present invention. The present invention is as follows.

[1] A micro-needle array including: a substrate; and a plurality of micro-needles arranged on one surface of the substrate, wherein tip parts of the plurality of micro-needles have a height difference, and the micro-needles have a needle length of 80 μm or more and 2000 μm or less.

The height difference of the tip parts of the micro-needles may be achieved by making the lengths of the plurality of micro-needles themselves standing on the substrate different, or may be achieved by further providing a substrate convex part on the substrate and erecting a plurality of micro-needles (the lengths may be the same) thereon. The height difference in the present invention can also be indicated by assuming that micro-needles having the same length are present on the substrate, and the tip parts of the micro-needles on the substrate convex part are higher than the tip parts of the micro-needles on the substrate.

[2] The micro-needle array according to [1], wherein the height difference of the plurality of micro-needles is based on non-uniformity of the needle length.

[3] The micro-needle array according to [1], wherein the height difference of the plurality of micro-needles is based on unevenness of the substrate.

[4] The micro-needle array according to [3], wherein arrangement of the plurality of micro-needles is unevenly distributed on the surface of the substrate, and is based on the fact that the unevenness of the substrate is high on the surface of the substrate on which the micro-needles are arranged and low on the surface of the substrate on which the micro-needles are not arranged.

[5] The micro-needle array according to [4], wherein the tip parts of the plurality of micro-needles arranged on a convex part of the substrate are higher than those of the plurality of micro-needles arranged on a concave part of the substrate.

[6] The micro-needle array according to [3], wherein arrangement of the plurality of micro-needles is unevenly distributed on the surface of the substrate, and is based on the fact that the unevenness of the substrate is high on the surface of the substrate on which the micro-needles are densely arranged and low on the surface of the substrate on which the micro-needles are sparsely arranged.

[7] The micro-needle array according to any one of [3] to [6], wherein the substrate has a circular surface, and has concentric unevenness, and a diameter (a) of a central convex part or concave part is greater than a width (b) of a peripheral concave part or convex part.

[8] The micro-needle array according to [7], wherein a relationship between the diameter (a) of the central convex part or concave part and the width (b) of the peripheral concave part or convex part is a≥2b.

[9] The micro-needle array according to any one of [3] to [8], wherein the substrate has a plurality of convex parts.

[10] The micro-needle array according to any one of [3] to [9], wherein the substrate has a plurality of concave parts, and the concave parts have the same height as that of the surface of the substrate.

[11] The micro-needle array according to any one of [3] to [9], wherein the substrate has a plurality of concave parts, and includes at least one recessed part higher than the surface of the substrate and lower than the convex part of the substrate.

[12] The micro-needle array according to [11], wherein the convex part includes a plurality of recessed parts, so that the plurality of convex parts are present.

[13] The micro-needle array according to any one of [3] to [12], wherein a height difference between the convex part and concave part of the substrate is 0.1 to 20 mm.

[14] The micro-needle array according to [13], wherein a height difference between the convex part and concave part of the substrate is 0.5 to 10 mm.

[15] A micro-needle array including: a substrate; and a plurality of micro-needles arranged on one surface of the substrate, wherein arrangement of the plurality of micro-needles is unevenly distributed on the surface of the substrate, and the surface of the substrate having a high needle density is higher in a direction of a needle length of the plurality of micro-needles than a surface of the substrate having a low needle density or having no needle, so that the substrate has unevenness.

[16] The micro-needle array according to [15], wherein the substrate has a circular surface, and has concentric unevenness, and a diameter (a) of a central convex part or concave part is greater than a width (b) of a peripheral concave part or convex part.

[17] The micro-needle array according to [16], wherein a relationship between the diameter (a) of the central convex part or concave part and the width (b) of the peripheral concave part or convex part is a≥2b.

[18] The micro-needle array according to any one of [15] to [17], wherein the substrate has a plurality of convex parts.

[19] The micro-needle array according to any one of [15] to [18], wherein the substrate has a plurality of concave parts, and the concave parts have the same height as that of the surface of the substrate.

[20] The micro-needle array according to any one of [15] to [19], wherein the substrate has a plurality of concave parts, and includes at least one recessed part higher than the surface of the substrate and lower than the convex part of the substrate.

[21] The micro-needle array according to [20], wherein the convex part includes a plurality of recessed parts, so that the plurality of convex parts are present.

[22] The micro-needle array according to any one of [15] to [21], wherein a height difference between the convex part and concave part of the substrate is 0.1 to 20 mm.

[23] The micro-needle array according to [22], wherein a height difference between the convex part and concave part of the substrate is 0.5 to 10 mm.

[24] A micro-needle array including: a substrate; and a plurality of micro-needles arranged on one surface of the substrate, wherein the substrate has the circular surface having an area of 0.5 to 5 $cm^2$, and has concentric unevenness, the plurality of micro-needles are arranged on the convex part, a diameter of a central concave part is larger than a width of a peripheral convex part, a height of the convex part from the surface of the substrate is 500 to 10000 μm, a needle length of the micro-needles is 80 to 900 μm, and the number of the needles is 100 to 1000/$cm^2$.

[25] A micro-needle patch including: the micro-needle array according to any one of [1] to [24]; and an adhesive sheet provided on the micro-needle array.

[26] The micro-needle patch according to [25], further including a release sheet attached to an adhesive surface of the adhesive sheet.

Effect of the Invention

The micro-needle array (for example, FIGS. 2A and 2B) of the first aspect of the present invention can be easily inserted into the skin as compared with the conventional micro-needle array (for example, FIG. 1B) in which the tip parts of the needles have the same height by applying the height difference to the tip parts of the needles.

In the micro-needle array (for example, FIG. 1A) according to the third aspect of the present invention, the provision of unevenness on the surface of the substrate makes it possible to reliably puncture the skin with a larger number of needles as compared with the micro-needle array (for example, FIG. 1B) in which the surface of the substrate forms the same plane, thereby further increasing the content of a drug per unit area and reliably delivering the drug transdermally.

In the micro-needle array (for example, FIGS. 3A, 3B, and 3C) according to the second aspect of the present invention, unevenness is provided on the surface of the substrate, and a height difference is applied to the tip parts of the needles between the concave part of the central part and the convex part of the peripheral part or between the convex part of the central part and the concave part of the peripheral part. This makes it possible to reliably puncture the skin with a larger number of needles as compared with the micro-needle array (for example, FIG. 1B) in which the surface of the substrate forms the same plane, thereby further increasing the content of the drug per unit area and reliably delivering the drug transdermally.

These effects were also verified in tests with parafilm and confirmed by transdermal administration to human volunteers. The reason is considered as follows. The outermost layer of the human skin is covered with a strong epidermis to respond to attack from the outside world. When the micro-needle array is administered by the applicator, the skin is tensioned and stretched by the compression of the needles, and then broken to insert the needles into the skin.

In the first aspect, by adjusting the lengths of the needles to provide the height difference to the tip parts of the needles, the high tip parts of the needles are more likely to be brought into contact with the skin than the low tip parts of the needles, so that skin tension when the micro-needle array is transdermally administered is higher than that when the needles are arranged at the same height because the degree to which the high tip parts of the needles bite into the skin during impact is higher. Accordingly, the assist of the insertion of the needles is considered to facilitate the insertion of the micro-needles into the skin.

In the second and third aspects, by providing unevenness on the surface of the substrate to easier bring the needles on the convex part of the surface of the substrate into contact with the skin, skin tension when the micro-needle array is transdermally administered is higher than that when the needles are arranged on the same surface of the substrate because the degree to which the surface of the substrate of the convex part bites into the skin during impact is higher. Accordingly, the assist of the insertion of the needles is considered to facilitate the insertion of the micro-needles into the skin.

In the third aspect, the concave part of the surface of the substrate does not substantially play an active role during skin administration, which may accordingly provide an aspect in which the concave part is eliminated. The aspect is shown in FIGS. 4C and 4D.

BRIEF DESCRIPTION OF THE DRAWINGS

FIG. 1 shows cross-sectional views schematically showing a product of the present invention (FIG. 1A) and a comparative product (FIG. 1B).

FIG. 2 shows cross-sectional views (FIGS. 2A, 2B) schematically showing a first aspect of the present invention.

FIG. 3 shows cross-sectional views (FIGS. 3A, 3B, 3C) schematically showing a second aspect of the present invention.

FIG. 4 shows a cross-sectional view (FIG. 4A) and a plan view (FIG. 4B) schematically showing a specific example of a third aspect of the present invention. FIG. 4 shows a cross-sectional view (FIG. 4C) and a plan view (FIG. 4D) of an aspect in which a concave part is eliminated.

FIG. 5 shows a cross-sectional view (FIG. 5A) schematically showing a third aspect of the present invention and a cross-sectional view (FIG. 5B) schematically showing a second aspect of the present invention. In both the aspects, needles are arranged so as to have a non-uniform needle density.

FIG. 6 shows a specific design view of the second aspect of the present invention (FIG. 6A) and a specific design view of the third aspect of the present invention (FIG. 6B). The width (a) of a central part and the width (b) of a peripheral part are designed such that a>b is set, and are designed such that a≥2b is set in FIG. 6B.

FIG. 7 shows a specific design view of the third aspect of the present invention. Although a cross-sectional view (FIG. 7A) is the same, two types of modifications in which convex parts of a substrate are not connected are shown in a plan view (FIGS. 7B and 7C). c represents the height of the convex part, and the convex part is designed to be 0.1 mm or more (FIG. 7D).

FIG. 8 shows a line drawing of a micro-needle array produced in Example 1.

FIG. 9 shows a line drawing of a micro-needle array produced in Comparative Example 1.

FIG. 10 shows a micrograph showing the shape of a needle of the micro-needle array produced in Example 1.

FIG. 11 shows a micrograph showing the shape of a needle of a micro-needle array produced in Example 2.

FIG. 12 shows a schematic view showing various forms of a micro-needle array of the present invention. FIG. 12(1) and FIG. 12(2) show a cross-sectional view and a plan view, and convex parts of a substrate on which micro-needles stand side by side at a constant density are fractionated by concave parts of a substrate having no micro-needles. FIG. 12(3) and FIG. 12(4) show variations of a substrate part where micro-needles stand side by side at a constant density.

FIG. 13 shows a schematic view showing various forms of a micro-needle array of Comparative Example. FIG. 13(1) shows a form in which micro-needles are arranged at a constant needle density on a substrate having a constant thickness without having unevenness. FIG. 13(2) shows a form in which micro-needles are arranged at a constant needle density on a convex part of a substrate having only the convex part. FIG. 13(3) shows a form in which micro-needles are arranged at a non-uniform needle density on a convex part of a substrate having only the convex part.

MODE FOR CARRYING OUT THE INVENTION

In the present invention, the terms “micro-needle”, “fine needle”, and needle are used interchangeably without particular distinction.

A micro-needle array of the present invention includes a substrate and a plurality of micro-needles arranged on one surface of the substrate. Tip parts of the plurality of micro-needles have a height difference.

Substrate of Micro-Needle Array

The material, shape, and size of the substrate of the micro-needle array are not particularly limited, and those conventionally used can be used.

The base of the substrate and the base of the micro-needle are basically the same, but may be different from each other.

Examples of the base include silicon, silicon dioxide, ceramic, glass, metals (stainless steel, titanium, nickel, molybdenum, chromium, and cobalt and the like), and synthetic or natural resin materials. Examples of the synthetic or natural resin material include water-soluble or biodegradable polymers such as polylactic acid, polyglycolic acid, a poly(lactic acid-glycolic acid) copolymer, capronolactone, polyurethane, polyvinylpyrrolidone, hydroxypropyl cellulose, and polyvinyl alcohol, and non-biodegradable polymers such as nylon, polycarbonate, polymethacrylic acid, ethylene vinyl acetate, polytetrafluoroethylene, polyoxymethylene, polyethylene terephthalate, and cyclic olefin polymer (COP). The base may also be a polysaccharide such as hyaluronic acid, sodium hyaluronate, a hyaluronic acid derivative, pullulan, dextran, dextrin, or chondroitin sulfuric acid. The base may be used alone or in combination of two or more thereof.

The substrate may have a surface having any shape. As an example, the shape may be a circle, an ellipse, a triangle, a quadrangle, or a polygon or the like as a basic shape, and may be further modified in accordance with the application site (skin). The size of the surface of the substrate is usually 0.2 to 10 cm, and preferably 0.5 to 5 cm, when represented by a diameter (long diameter) or a length of one side (long side).

The area of the surface of the substrate is usually 0.05 to 100 $cm^2$. From the viewpoint of ease of handling, the area is preferably about 0.1 to 10 $cm^2$, and more preferably about 0.5 to 5 $cm^2$.

The thickness of the substrate is represented by the length of the cross-section in the direction of the needle length of the micro-needle to be arranged. The entire thickness of the substrate having unevenness is usually 0.3 to 25 mm, and preferably 0.6 to 15 mm although it depends on the material of the base.

A height difference between the convex part and concave part of the substrate (height indicated by c in FIG. 7D) is usually 0.1 to 20 mm, and preferably 0.5 to 10 mm.

When the substrate has a circular surface, the substrate can have concentric unevenness. In this case, the diameter (a) of a central convex part or concave part is preferably greater than the width (b) of a peripheral convex part or concave part.

The relationship between the diameter (a) and the width (b) is more preferably a≥2b from the viewpoint that the central part of the skin is recessed more largely than the periphery, which causes difficult needle insertion.

When the surface of the substrate has a quadrangular shape or a polygonal shape or the like, a convex part may be provided on the outer periphery, and a concave part may be provided inside the convex part.

A plurality of convex parts and concave parts may be present on one substrate.

The plurality of concave parts may have the same height as that of the surface of the substrate, and may include at least one recessed part higher than the surface of the substrate and lower than the convex part. When a plurality of recessed parts are present, and the convex part includes the plurality of recessed parts, a plurality of divided convex parts may be provided.

The height of the recessed part needs to be set to 100 μm or more and 10,000 μm or less from the surface of the substrate from the viewpoint of skin tension during pressing.

Shape of Micro-Needle

A micro-needle included in the micro-needle array has a needle length of 80 μm or more and 2,000 μm or less, and preferably 150 to 1,000 μm in order to ensure transdermal absorption of a drug.

When the size of the apex of the tip part of the needle is represented as a diameter, the diameter is 80 μm or less, and preferably 40 μm or less, in order to facilitate insertion into the skin and reduce the drug residue on the skin.

Each micro-needle has a cylinder or circular cone shape with a circular bottom surface, an elliptic cylinder or elliptic cone shape with an elliptic bottom surface, a triangular prism or triangular pyramid shape with a triangle bottom surface, a quadrangular prism or quadrangular pyramid shape with a quadrangular bottom surface, and a polygonal prism or polygonal pyramid shape with a polygonal bottom surface. In the case of an ellipse, the size of the bottom surface is represented by a major axis as a diameter, and the minor axis is shorter than the major axis as long as an ellipse can be formed. In the case of a triangle or a polygon, one side may be represented as the size, or a diagonal line may be represented as the size. When the micro-needle has a circular cone shape, the diameter at the bottom surface is about 100 to 400 μm and preferably about 150 to 300 μm. The needle shape is preferably sharp considering skin insertion, and the aspect ratio is preferably 1 or more, and more preferably 2 or more.

The micro-needle in the present invention may have a step. Here, the step refers to a portion where the cross-sectional area of the micro-needle is discontinuously reduced from a certain point of the micro-needle toward the tip and where a cross section has a stepwise shape as shown in FIGS. 10 and 11. In the stepped micro-needle, it is preferable that the length of a tip part is 50 to 500 μm and the rest is defined as a bottom part. The size of the margin of the step between the tip part and the bottom part is preferably more than 10 μm and less than 100 μm. The size is more preferably 14 to 50 μm.

The margin of the step is a surface orthogonal to the axis of the micro-needle (surface parallel to the substrate) within the range of machining accuracy. The size of the margin of the step refers to a difference in radius between the tip part and the bottom part of the step. The tip part and the bottom part differ depending on the shape of the micro-needle.

As a preferred aspect, the micro-needle of the present invention has a circular cone shape, but the shape may be a quadrangular pyramid or a triangular pyramid or the like. The total length (needle length) of the micro-needle is preferably about 80 to 1000 μm. In the stepped micro-needle, it is preferable that the length of the tip part is 50 to 500 μm and the rest is defined as the bottom part (two-step needle), or the rest is defined as an intermediate part and the bottom part in a three-step needle. The size of the margin of the step between the tip part and the intermediate part and between the intermediate part and the bottom part is preferably more than 10 μm and less than 100 μm. The size is more preferably 14 to 50 μm.

Arrangement of Micro-Needles on Substrate

The micro-needle array of the present invention may have a uniform needle density when the entire surface of the substrate is viewed from the upper surface. A micro-needle array having an area with needles and an area without needles has a non-uniform needle density.

The micro-needle array of the present invention includes a substrate and a plurality of micro-needles arranged on one surface of the substrate. Tip parts of the plurality of micro-needles have a height difference.

In a first aspect of the micro-needle array of the present invention, the height difference of the plurality of micro-needles is based on the non-uniformity of the lengths of the needles.

In a second aspect of the micro-needle array of the present invention, the height difference of the plurality of micro-needles is based on the unevenness of the substrate on which the needles are arranged. In this case, the lengths of the needles may be uniform or non-uniform.

In a third aspect of the micro-needle array of the present invention, arrangement of the plurality of micro-needles is unevenly distributed on the surface of the substrate, and is based on the fact that the unevenness of the substrate is high on the surface of the substrate on which the micro-needles are arranged and low on the surface of the substrate on which the micro-needles are not arranged.

The third aspect may be based on the fact that arrangement of the plurality of micro-needles is unevenly distributed on the surface of the substrate, and the unevenness of the substrate is high on the surface of the substrate on which the micro-needles are densely arranged and low on the surface of the substrate on which the micro-needles are sparsely arranged. In the present invention, the fact that the micro-needles are sparsely arranged is a concept including the presence of a portion where no micro-needles are present (the number of needles is 0). In this case, due to the presence of the concave part where no micro-needles are present (the number of needles is 0), the tip parts of the micro-needles on the convex part where the micro-needles are densely arranged may have no height difference (for example, FIGS. 1A, 4, 5A, 6B, 7, and 8).

The present aspect also includes a micro-needle array having no substrate in a central part. That is, the micro-needle array is also called a doughnut type or a perforated coin type. The central part may be a separate substrate concave part separated from the periphery, but there may be a concave part having no needles directed outward from the central part. This portion is referred to as a corridor part (for example, a concave part 4 in the lower right view of FIG. 12(1)).

It is preferable that the needle density of the micro-needles is sparser in the central part than in the peripheral part of the substrate from the viewpoint of reliable skin puncturability of the needles.

As a suitable example, the needle density of the micro-needles is 50 to 1500 needles/cm$^2$, and more preferably 100 to 1000 needles/cm$^2$. It is preferable that the micro-needles in the present invention are arranged to be concentrated in a base part (which is the convex part of the substrate, and is preferably located in the peripheral part of the substrate). The micro-needles may be present in the substrate part, the central part, and the corridor part, but the needle density is made smaller than that of the base part. Specifically, the needle density is 0 to 149 needles/cm$^2$.

The needle interval of the micro-needles can be appropriately set from the ratio between the area of the central part and the area of the peripheral part of the substrate, and the needle density of the micro-needles. The needle density may be set such that the interval of the needles satisfies ≥200 μm. The interval more preferably satisfies ≥300 μm. The array of the needles is a square array, a triangular array, or a parallelogram array of the like, but is not limited thereto.

When the surface of the substrate is a circle, it is preferable that the central part of the substrate is inside a circumference of ½, ⅔, or ⅔ or less of the radius from the center of the circle, and the peripheral part of the substrate is outside the central part based on the observation result of the region where the skin insertion of the micro-needle array is difficult. The base part is installed at such a position to cause the micro-needles to stand.

Preferred Aspect of Micro-Needle Array

A preferred aspect of the micro-needle array of the present invention has the following features:

- the substrate has a circular surface having an area of 0.5 to 5 cm$^2$ and concentric unevenness;
- the plurality of micro-needles are arranged on the convex part;
- the diameter of the central concave part is more than the width of the peripheral convex part, and the height of the convex part from the surface of the substrate is 500 to 10000 μm; and
- the micro-needles have a needle length of 80 to 900 μm, and the number of needles is 100 to 1000 needles/cm$^2$.

Suitable specific examples thereof include those produced in Examples 1 to 3.

Micro-Needle Patch

The micro-needle patch of the present invention may include the micro-needle array and an adhesive sheet. The adhesive sheet is typically obtained by using polyurethane, polyethylene, polyester, or paper or the like as a base material of a film, and applying an acrylic or rubber-based adhesive of about 5 to 100 μm onto a film molded to have a thickness of about 5 to 50 μm. The shape of the adhesive sheet is not particularly limited, and is preferably a circle, an ellipse, a bead, or a quadrangle or the like similar to the shape of the micro-needle array.

The micro-needle patch of the present invention may further include a release sheet attached to the adhesive surface of the adhesive sheet so as to protect the adhesive surface of the adhesive sheet and hold a flexible micro-needle array for easy handling.

As the release sheet, a known release sheet can be used. For example, a protective release sheet disclosed in JP 2014-028108 A can also be used.

Drug Held by Micro-Needles

The micro-needle array of the present invention may contain a drug in a base when the base of the micro-needle is a water soluble polymer. Alternatively, the micro-needle array of the present invention may have a drug application layer at the tip part of the micro-needle, and the material of the needle part in this case may be a water soluble polymer or an insoluble plastic.

Here, the drug includes all compounds that act on the skin or penetrate the skin and produce some beneficial action. Examples of the drugs suitable for the purpose of the present invention include physiologically active peptides and derivatives thereof, nucleic acids, oligonucleotides, various antigenic proteins, bacteria, and viral fragments. Examples of the physiologically active peptides and derivatives thereof include calcitonin, adrenocorticotropic hormone, parathyroid hormone (PTH), hPTH (1→34), insulin, exendin, secretin, oxytocin, angiotensin, β-endorphin, glucagon, vasopressin, somatostatin, gastrin, luteinizing hormone releasing hormone, enkephalin, neurotensin, atrial natriuretic peptide, growth hormone, growth hormone releasing hormone, bradykinin, substance P, dynorphin, thyroid-stimulating hormone, prolactin, interferon, interleukin, G-CSF, glutathione peroxidase, superoxide dismutase, desmopressin, somatomedin, endothelin, and salts thereof. Examples of the antigenic proteins include viral antigen proteins of influenza antigens, HBs surface antigens, and HBe antigens.

The drug may be a cosmetic product.

In the case of the micro-needle array in which the base of the micro-needle is the water-soluble polymer and the drug is contained in the base, the concentration of the drug in the base is 0.1% by mass or more and 90% by mass or less, preferably 0.5% by mass or more and 80% by mass or less, and more preferably 1.0% by mass or more and 60% by mass or less.

In the case of a micro-needle array having a drug application layer at the tip part of a micro-needle, the lower end of the drug application layer may be 50 μm or more from the root of the needle, and the upper end may have any height depending on the application amount of the drug. Preferably, the upper end is the tip of the micro-needle, but the drug does not necessarily have to be applied up to the tip. The length of the drug application layer is typically 40 μm or more and 800 μm or less, and preferably 150 μm or more and 600 μm or less.

The lower end and the upper end of the drug application layer are values obtained by respectively measuring the lower end and the upper end of the micro-needle to which the drug is applied in the vertical direction from the substrate of the micro-needle array. The length of the drug application layer is represented by the difference between the lower end and the upper end of the micro-needle to which the drug is applied.

Meanwhile, the thickness of the drug application layer varies depending on the drug application liquid and the number of times of application.

When the tip of the micro-needle is immersed in a drug aqueous solution to apply a drug to the tip of the micro-needle, it is desirable that a base material substance is dissolved in the drug aqueous solution, and the drug is held by the micro-needle together with the base material substance when the drug is dried after application. The base material substance is required to be a substance that does not impair the stability of the drug, and examples thereof include: polymer substances, for example, polymeric polysaccharides such as hyaluronic acid, dextrin, dextran, chondroitin sulfate sodium, hydroxypropyl cellulose, ethyl cellulose, and carboxymethyl cellulose sodium salt, proteins such as collagen, water-soluble synthetic polymers such as polyvinyl pyrrolidone and polyvinyl alcohol; low molecular weight saccharides such as glucose, sucrose, maltose, and trehalose; and mixtures thereof. A drug aqueous solution to which the base material substance and a water-soluble salt are added is suitable.

Here, the water-soluble salt is suitably a water-soluble salt such as sodium chloride or zinc chloride.

The concentration of the base material substance in the drug aqueous solution is desirably 2% by mass to 60% by mass. When the concentration is lower than 2% by mass, the viscosity of the drug aqueous solution is small, and the application adhesion amount at the time of immersion is small. When the concentration is 60% or more, the concentration of the drug aqueous solution is too high, and drug application is not stable. The ratio of the polymer and the low molecular weight saccharide in the base material may be changed depending on the properties of the drug. When the drug is a polymer drug, all of the base may be a low molecular weight saccharide.

An antioxidant or a surfactant or the like may be added to the aqueous drug solution as necessary. Glycerin, ethylene glycol, and a low molecular weight polymer thereof may be added to further enhance the dissolution of the drug in the skin.

Method for Producing Micro-Needle Array (1) Processing of Die

The die used for producing the micro-needle array of the present invention may be produced by wet etching processing or dry etching processing using a silicon substrate, precision machining (electrical discharge machining, laser machining, hot embossing, or injection molding or the like) using metal or resin, or machine cutting processing or the like.

(2) Step of Molding Micro-Needle Array

A micro-needle array made of a water-soluble polymer may be mass-produced using a mold (die). Examples thereof include a method for casting an aqueous solution containing a water-soluble polymer, and a drug and other components as necessary, drying the aqueous solution, thereafter peeling off the resulting product (JP 2009-273872 A [0031] to [0033]). The base of the substrate and the base of the micro-needle are basically the same, but may be different from each other. In the molding of the micro-needle in this case, an appropriate amount of an aqueous solution containing a drug and other components is cast into a mold, and dried to mold a micro-needle part. Thereafter, an aqueous solution or an organic solvent in which a base different from the base of the micro-needle part is dissolved is cast, and dried to form a substrate part.

A micro-needle made of a polymer that can be injection-molded may be produced by injection-molding a material using a die (JP 2003-238347 A [0017] and [0018]). As the injection molding die, stainless steel, heat-resistant steel, or superalloy or the like may be used. The die has concave parts corresponding to 100 to 1500 micro-needles per square centimeter to form the shape of the micro-needles. In order to form the concave parts, micro-machining means such as laser or electrical discharge machining may be used.

One aspect of a method for producing a micro-needle array made of a polymer that can be injection-molded (for example, thermoplastic resin) is a method for supplying pellets made of a thermoplastic resin material to an injection molding machine equipped with a micro-needle injection molding die, and injection-molding a micro-needle array at a cylinder temperature of 230 to 280 °C, a die temperature of 60 to 130 °C, and an injection pressure of 1000 to 1500 kPa.

As the thermoplastic resin material, polyglycolic acid, polylactic acid, or a copolymer thereof may be used alone or as a mixture. Furthermore, a composition containing an inorganic filler and another thermoplastic resin and the like may be used as long as the object of the present invention is not impaired.

As a suitable specific example, a composition (compound) obtained by blending 0 to 20 parts by mass of an inorganic filler and 0 to 30 parts by mass of another thermoplastic resin and the like with respect to 100 parts by mass of polyglycolic acid may be used. If the amount of the inorganic filler or the other thermoplastic resin is more than 20 parts by mass, the resulting injection molded product may be insufficient in impact strength and toughness, and melt processability may deteriorate.

Examples of the inorganic filler include silica, titanium oxide, calcium carbonate, and calcium silicate. These may be used singly or in combination of two or more kinds thereof.

Examples of the other thermoplastic resin include homopolymers and copolymers of ε-caprolactone, and TPX. These thermoplastic resins may be used singly or in combination of two or more kinds thereof. The other thermoplastic resin is usually used at a ratio of 0 to 30 parts by mass with respect to 100 parts by mass of polyglycolic acid, for example.

The micro-needle array obtained by injection molding is taken out from the die after cooling.

The taken-out micro-needle array can apply the drug to the tip part of the needle, as described above. For example, the drug can be applied using a micro-needle application liquid described in JP 2017-137311 A or JP 2018-108375 A.

EXAMPLES

Examples of the present invention are shown below, but the present invention is not limited to Examples.

Example 1

A die was attached to an injection molding machine (FANUC CORPORATION), and polyglycolic acid was melted to perform injection molding. The injection molding was performed at a cylinder temperature of 235 °C, an injection pressure of 1350 kPa, and a die temperature of 120 °C, and a milky white elliptical micro-needle array was taken out. The array had a major axis of 12.3 mm and a minor axis of 11.5 mm (FIG. 8).

The details of the present micro-needle array are as follows.

Outer diameter of base part (convex part) on which needles on substrate of array stand: 10.5 mm, inner diameter of base part (convex part): 6.00 mm, width of corridor part: 1.2 mm, heights of corridor part and central part (concave part) from surface of substrate: 0.5 mm, height of surface of base part (convex part): 1.3 mm, needle length: 0.6 mm, total number of needles: 280 (FIG. 10).

Example 2

A micro-needle array was produced in the same manner as in Example 1 except that a needle length was 0.9 mm (FIG. 11).

Example 3

A micro-needle patch was produced in the same manner as in Example 1 except that the inner diameter of a base part (convex part) was 7.00 mm, a needle length was 0.9 mm, and the total number of needles was 230.

Comparative Example 1

A die was attached to an injection molding machine (FANUC CORPORATION), and polyglycolic acid was melted to perform injection molding. The injection molding was performed at a cylinder temperature of 235 °C, an injection pressure of 1350 kPa, and a die temperature of 120 °C, and a milky white micro-needle array having a diameter of about 10 mm was taken out. The array had a major axis of 12.3 mm and a minor axis of 11.5 mm (FIG. 9).

The details of the present micro-needle array are as follows.

Outer shape of base part (convex part) on which needles on substrate of array stand: 10.5 mm, needles are provided on outer periphery of base part (convex part), no needles are provided within inner diameter of 6.00 mm, height of surface of base part (convex part): 1.3 mm, needle length: 0.6 mm, total number of needles: 310.

Comparative Example 2

A micro-needle patch was produced in the same manner as in Comparative Example 1 except that needles were uniformly provided on the entire surface of a base part (convex part) and the total number of the needles was 190 in Comparative Example 1.

Comparative Example 3

An aqueous hyaluronic acid solution obtained by dissolving 4 parts by mass of a high molecular weight hyaluronic acid having a weight average molecular weight of 100,000 (trade name: FUH-SU, manufactured by Kikkoman Biochemifa Company) in 96 parts by mass of water was cast on a mold, dried, and molded to obtain a micro-needle array. The micro-needle array was a type in which micro-needles stood side by side on a substrate and the substrate had no height difference. The micro-needles had a truncated cone shape with a micro-needle length of 0.8 mm, a root diameter of 0.2 mm, and a tip diameter of 0.03 mm. The micro-needles were uniformly arranged in a lattice manner with an interval therebetween of 0.8 mm. The substrate had a circular shape. The total number of needles was 120.

Test Example 1 Administration Test of Micro-Needle Array to Laminated Parafilm Skin Model The present micro-needle arrays of Examples 1 to 3 and Comparative Examples 1 to 3 were attached to a spring type applicator. The spring constant of the applicator was 0.516 N/mm$^2$. Five parafilms (manufactured by LMS, thickness: 170 μm) were stacked on a silicon plate having a thickness of 1 cm to form a skin model, and the micro-needle array was impact-administered thereon using the applicator. The micro-needle array was peeled off from the parafilms, and the penetration state of the needles at the fourth parafilm from the surface was observed with a microscope. In the case where the needles penetrate the fourth parafilm, it is predicted that the needles reach a depth of approximately 520 μm from the skin. Two examples were performed for each group, and the average achievement ratio was determined. The results are shown in Table 1.

TABLE 1

| Working sample group | Total number of needles | Achievement ratio of 520 μm of needle (%) |
|---|---|---|
| Example 1 | 280 | 98 |
| Example 2 | 280 | 100 |
| Example 3 | 230 | 100 |
| Comparative Example 1 | 310 | 55 (central needle part is unachieved) |
| Comparative Example 2 | 190 | 32 (central needle part is unachieved) |
| Comparative Example 3 | 120 | 20 (central needle part is unachieved) |

In Comparative Examples 1 and 2, the surface on which the needles stand (the plane of the needle of the convex part) is higher than the plane of the substrate, but does not have a central part or corridor part (concave part) of the recessed substrate. Comparative Example 1 is a micro-needle array having a needle density difference, but Comparative Example 2 is a micro-needle array having no needle density difference. Both the arrays had a diameter of 10.5 mm. As in Examples, by setting the micro-needles also on the central part and the corridor part (concave part) of the recessed substrate, the result of predicting that the skin was reliably punctured with more needles was obtained.

Example 4

The tips of the micro-needles produced in Examples 1 and 2 and Comparative Example 1 were impregnated and coated with an aqueous solution containing 0.02% by mass of resveratrol as a model compound for quantification, 2% by mass of carboxymethyl cellulose as a solid base, and 15% by mass of Dextran 70. Thereafter, the resveratrol-containing solid was applied to the tip part by drying. All the reagents were purchased from Wako Pure Chemical Industries, Ltd. By adjusting application conditions, 0.5 to 0.6 mg of the solid was applied onto each micro-needle array.

The micro-needle array was administered to the upper arm of each of four human volunteers by an applicator, and collected after 1 hour. The collected array was immersed in ethanol to recover the remaining resveratrol in the ethanol. The concentration of the remaining resveratrol was quantified by HPLC and fluorescence detection, and the ratio of the resveratrol transferred into the body was calculated. HPLC conditions are shown below.

The obtained results are shown in Table 2.

TABLE 2

| Administered micro-needles | Amount transferred into body (%) ((Application amount − remaining amount)/application amount) × 100 | | | |
|---|---|---|---|---|
| Example 1 | 96.8 | 96.5 | 92.3 | 95.9 |
| Example 2 | 97.7 | 96.3 | 96.1 | 97.4 |
| Comparative Example 1 | 75.5 | 82.4 | 79.9 | 71.7 |
| Comparative Example 2 | 66.2 | 64.5 | 67.3 | 56.1 |

Resveratrol Quantification Conditions

Column: Shiseido ODS type column 4.6 mm I.D.×250 mm

Detection (fluorescence): Excitation wavelength 300 nm, fluorescence wavelength 386 nm Moving layer: 0.2% formic acid water/acetonitrile=72:28 solution (vol %)

From Table 2, it was found that the micro-needle arrays of Examples are more excellent in transdermal transfer of drugs than the micro-needle arrays of Comparative Examples.

DESCRIPTION OF REFERENCE SYMBOLS

1 Micro-needle
2 Substrate
3 Convex part of substrate
4 Concave part of substrate

The invention claimed is:

1. A micro-needle array comprising:
a substrate; and
a plurality of micro-needles arranged on one surface of the substrate,
wherein
arrangement of the plurality of micro-needles is unevenly distributed on the surface of the substrate, and
the surface of the substrate having a high needle density is higher in a direction of a needle length of the plurality of micro-needles than the surface of the substrate having a low needle density or having no needle, so that the substrate has a convex part and a concave part, and
wherein a height difference between the convex part and the concave part of the substrate is 0.1 to 20 mm.

2. The micro-needle array according to claim 1,
wherein
the substrate has a circular surface, and has concentric unevenness, and
a diameter (a) of a central convex part or concave part is greater than a width (b) of a peripheral concave part or convex part.

3. The micro-needle array according to claim 2, wherein a relationship between the diameter (a) of the central convex part or concave part and the width (b) of the peripheral concave part or convex part is a≥2b.

4. The micro-needle array according to claim 1, wherein the substrate has a plurality of convex parts.

5. The micro-needle array according to claim 1, wherein the substrate has a plurality of concave parts, and the concave parts have the same height as that of the surface of the substrate.

6. The micro-needle array according to claim 1, wherein the substrate has a plurality of concave parts, and includes at least one recessed part higher than the surface of the substrate and lower than the convex part of the substrate.

7. The micro-needle array according to claim 6, wherein the substrate includes a plurality of recessed parts, so that the plurality of convex parts are present.

8. The micro-needle array according to claim 1, wherein the height difference between the convex part and the concave part of the substrate is 0.5 to 10 mm.

9. The micro-needle array according to claim 1,
wherein
the substrate has a circular surface having an area of 0.5 to 5 $cm^2$, and has the convex part and the concave part arranged concentrically,
the plurality of micro-needles are arranged on the convex part,
a diameter of a central part of the concave part is larger than a width of a peripheral part of the convex part,
a height of the convex part from the surface of the substrate is 500 to 10000 μm,
a needle length of the micro-needles is 80 to 900 μm, and
the number of the needles is 100 to 1000/$cm^2$.

10. A micro-needle patch comprising:
the micro-needle array according to claim 1; and
an adhesive sheet provided on the micro-needle array.

11. The micro-needle patch according to claim 10, further comprising a release sheet attached to an adhesive surface of the adhesive sheet.

* * * * *